United States Patent
Retterath et al.

(10) Patent No.: US 6,829,927 B2
(45) Date of Patent: Dec. 14, 2004

(54) SYSTEM FOR CONTENT ANALYSIS OF COMESTIBLE PRODUCTS USING VOLUMETRIC DETERMINATION

(75) Inventors: James E. Retterath, Excelsior, MN (US); Robert A. Laumeyer, Minneapolis, MN (US); Steven A. Chapman, Eden Prairie, MN (US)

(73) Assignee: Facet Technology Corp., Eden Prairie, MN (US)

( * ) Notice: Subject to any disclaimer, the term of this patent is extended or adjusted under 35 U.S.C. 154(b) by 68 days.

(21) Appl. No.: 10/462,456

(22) Filed: Jun. 16, 2003

(65) Prior Publication Data

US 2004/0035198 A1 Feb. 26, 2004

Related U.S. Application Data

(62) Division of application No. 10/226,640, filed on Aug. 23, 2002, now Pat. No. 6,609,423.

(51) Int. Cl.[7] .............................................. G01F 17/00
(52) U.S. Cl. ........................................................ 73/149
(58) Field of Search ........................... 73/866, 149, 433

(56) References Cited

U.S. PATENT DOCUMENTS

| | | | |
|---|---|---|---|
| 3,282,115 A | 11/1966 | Taylor et al. | |
| 3,455,168 A | 7/1969 | Taylor et al. | |
| 3,487,698 A | 1/1970 | Leger et al. | |
| 4,369,652 A | * 1/1983 | Gundlach | 73/149 |
| 4,449,406 A | 5/1984 | van Haren | |
| 4,813,101 A | 3/1989 | Brakels et al. | |
| 5,077,477 A | 12/1991 | Stroman et al. | |
| 5,105,825 A | 4/1992 | Dempster | |
| 5,326,311 A | 7/1994 | Persoon et al. | |
| 5,450,750 A | 9/1995 | Abler | |

OTHER PUBLICATIONS

Website print–out: *Introduction to Sensors*, C.D.H. Williams, University of Exeter School of Physics, 9 pgs., Aug. 23, 2002.

Website print–out: *Pressure Sensors and Instruments*, http://www.globalspec.com, 1 pg., Aug. 23, 2002.

Website print–out: *Sensors Business Digest: Sensor Industry Developments and Trends*, Peter Adrian, Ed., 3 pgs., Sep. 1999.

Website print–out: *Pressure Transducers*, http://www.transicoil.com, 2 pgs., Aug. 23, 2002.

Website print–out: *Industrial Waste Water Monitoring*, http://www.alfadhlitrading.com, 5 pgs., Aug. 23. 2002.

* cited by examiner

*Primary Examiner*—Robert Raevis
(74) *Attorney, Agent, or Firm*—Patterson, Thuente, Skaar & Christensen, P.A.

(57) ABSTRACT

A system that performs content analysis on comestible products using volumetric determination with a single-chamber technique in a mass production environment. The content value determination system includes a conveyor system, a system for weighing the comestible products interposed along the path of the conveyor, a volumetric determination station that consists of a plurality of receiving chambers, and a control module. In this embodiment, each receiving chamber is equipped with a pressure sensor and a mechanical system for modifying the volume of the chamber. In addition, both the pressure sensors and the volume modification system of each receiving chamber are operably connected to the control module.

2 Claims, 2 Drawing Sheets

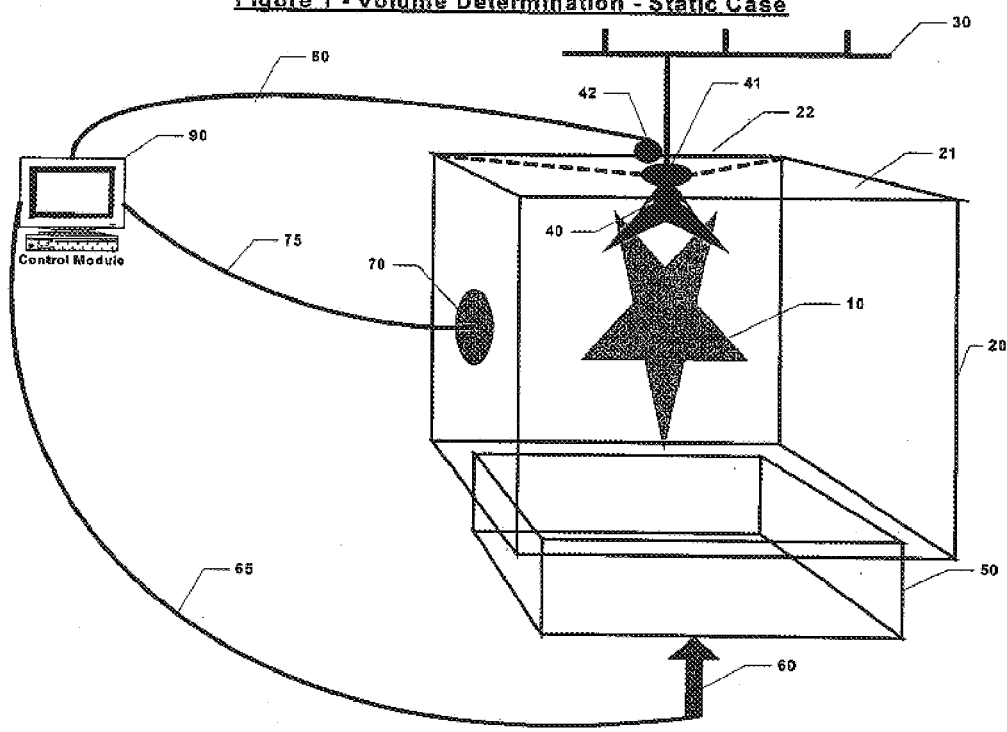

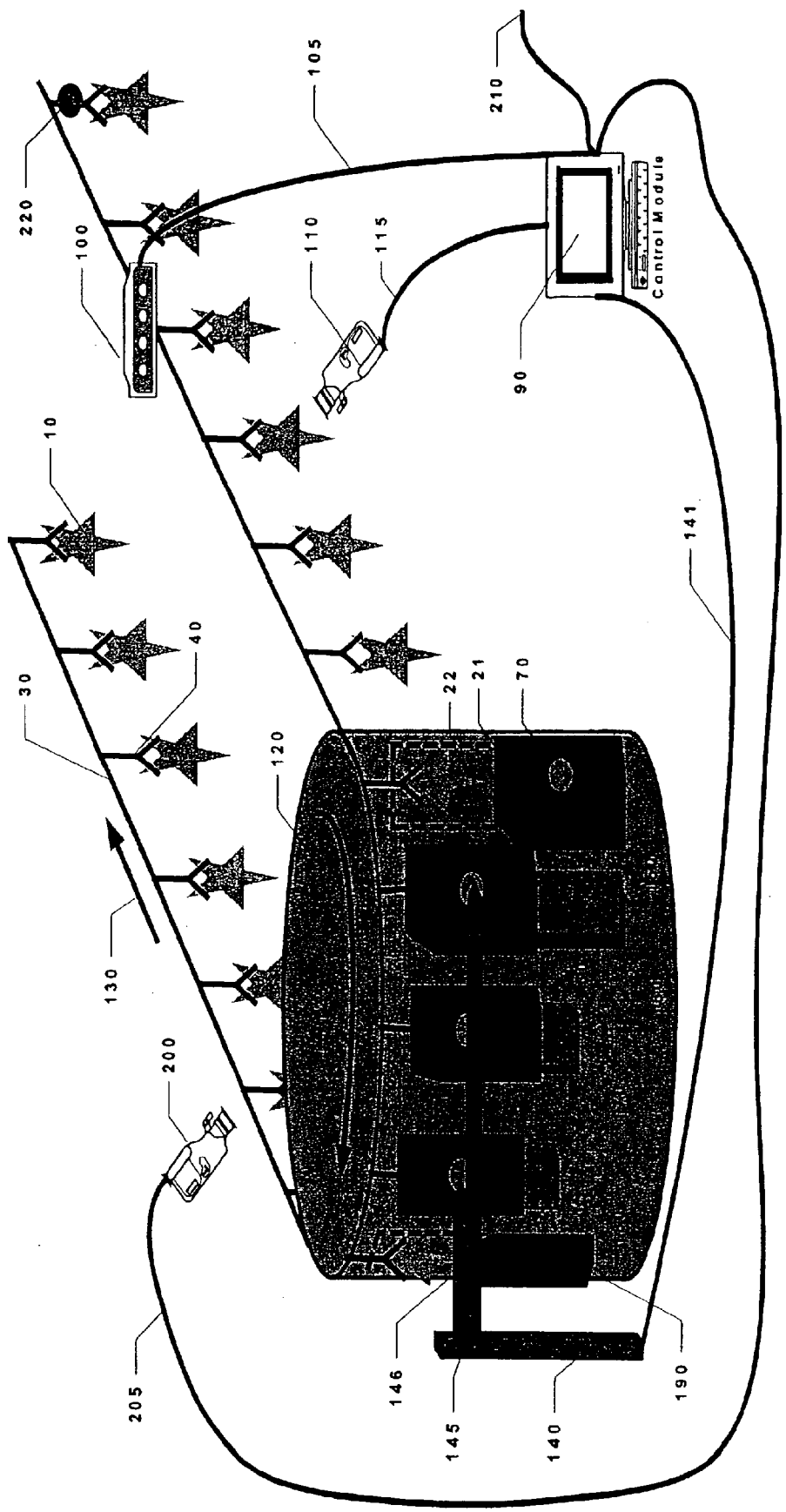

US 6,829,927 B2

SYSTEM FOR CONTENT ANALYSIS OF COMESTIBLE PRODUCTS USING VOLUMETRIC DETERMINATION

RELATED APPLICATIONS

This application is a divisional of U.S. patent application Ser. No. 10/226,640, now U.S. Pat. No. 6,609,423, filed Aug. 23, 2002, entitled "SYSTEM FOR CONTENT ANALYSIS OF COMESTIBLE PRODUCTS USING VOLUMETRIC DETERMINATION," the disclosure of which is hereby incorporated by reference.

FIELD OF THE INVENTION

The present invention is related to the field of volume determination of comestible products, i.e., meat cuts and whole animal carcasses. More specifically, the present invention is directed towards methods and devices for the automated high-speed volumetric determination of content values, including fat content, in various comestible products.

BACKGROUND OF THE INVENTION

Meat, poultry and fish producers are in the business of converting live animals into consumable products for humans. These producers experience thin profit margins and are constantly in search of processes that can increase the quality of the product offered to consumers.

One attribute that determines processed food quality is fat content. For most meat, poultry and fish products for example, reduced-fat cuts are more desirable and, as such, more profitable for the producers. Unfortunately, fat content for whole animal products or for processed animal parts is difficult to determine since most of the contained fat is not exposed at the surface of the whole animal carcass or processed cut. The industry needs a reliable way of determining fat content for processed meat, fish and poultry without subjecting the cut or carcass to destructive processes.

It is relatively easy to precisely measure the weight (and determine the mass) of meat, poultry and fish. Since fat and lean densities are well known in these industries, the percentage of fat content can be precisely determined if the exact volume of the cut or carcass could be measured. Unfortunately, the industry has not been able to realize a reliable approach for performing non-contact, non-destructive volumetric measurement, particularly in a mass production environment.

Previous methods for determining the fat content of cuts of meat required measuring the volume of the cuts of meat by compressing the tissue to a preselected state and directly measuring the volume. More specifically, these previous methods generally used a piston or a press plate to apply a substantial force to the meat sample in order to compact the meat sample and measure the volume. Examples are shown in U.S. Pat. Nos. 3,282,115 to Taylor et al.; 3,455,168 to Taylor et al.; U.S. Pat. No. 3,487,698 to Leger et al.; and U.S. Pat. No. 4,449,406 to van Haren. There are several drawbacks to these previous approaches for determining the volume of a meat sample. For example, the previous methods are time-consuming, are not well suited for modern automated food production facilities and do not provide a non-contact means for measuring the volume of the comestible product. In addition, these methods do not accurately measure the volume of every cut of meat, nor do they provide a means for determining the volume, and ultimately the fat content, of a whole animal carcass.

Another volumetric method for determining the fat content of an object consists of two connected chambers. In this method, the object to be measured is enclosed in the first chamber, which is connected to a second chamber of known volume. Pressure measurements are then made in the chamber housing the object both before and after a valve is opened connecting the two chambers. Knowing the two pressures and the incremental volume of the second chamber allows one to calculate the volume of the object in the first chamber by Boyle's law. Examples of these two chamber techniques are shown in U.S. Pat. Nos. 5,105,825 to Dempster and U.S. Pat. No. 5,450,750 to Abler.

While a two-chamber approach to volumetric measurement can be a useful way to compute the volume and ultimately the fat content, of human subjects, this approach does not lend itself to the high-speed requirements of modern food processing facilities because of cost and space issues. The two-chamber approach is simply not feasible for mass production facilities because each measurement chamber requires a second connected chamber of known volume. With the large number of comestible products being produced, it would be desirable to provide an automated high-speed system for determining the volume, and ultimately the fat or other content values, of comestible products that address these and other shortcomings of the existing techniques.

SUMMARY OF THE INVENTION

The present invention is a system that performs content analysis on comestible products using volumetric determination with a single chamber technique in a mass production environment. The content value determination system includes a conveyor system, a system for weighing the comestible products interposed along the path of the conveyor, a volumetric determination station that consists of a plurality of receiving chambers, and a control module. In this embodiment, each receiving chamber is equipped with a pressure sensor and a mechanical system for modifying the volume of the chamber. In addition, both the pressure sensors and the volume modification system of each receiving chamber are operably connected to the control module.

In a preferred embodiment, the system includes an X-ray emitter and collector that provide X-ray images as the comestible products move along the path of the conveyor. The X-ray emitter and collector are operably connected to the control module, where the X-ray images are stored and used to determine the percentage of each comestible product that is bone material. This feature of the invention improves the overall accuracy of the content value determination for boned objects.

In another embodiment of the present invention, a volumetric determination device is provided. The volumetric determination device includes a single selectively sealable volumetric measurement chamber designed to enclose a comestible food product, such as a meat cut or whole animal carcass. The volumetric measurement chamber is equipped with a pressure sensor that is operably coupled to a control module. The pressure sensor measures the pressure inside the volumetric measurement chamber both before and after the volume inside the chamber has been modified by a known amount. A mechanical system is operably connected to the volumetric measurement chamber and provides a method for changing the volume of the chamber. In this embodiment, the volume of the comestible product can be computed by the control module based upon the initial pressure inside the chamber, the final pressure and the known change in volume of the chamber.

In a method in accordance with the present invention, a content value of a comestible product is determined by an automated process. The comestible products are placed onto a conveyor system. While moving along the conveyor system, the comestible products are weighed by a weighing system interposed along the path of the conveyor. The weighing system is operably connected to a control module, which records the weight of each comestible product. The conveyor system transports the comestible products to a volumetric determination station that consists of multiple receiving chambers. Each individual comestible product is encompassed in one of the receiving chambers and the initial pressure inside the chamber is recorded. The volume of the chamber is then modified by a known amount by a mechanical system and a second pressure is recorded. The control module, which is operably connected to each receiving chamber, then computes the volume of each of a plurality of comestible products based upon the change in pressure inside the chambers and the known modified volume. Once the volume of the comestible product is known, the control module can compute the fat content, or other content values, of the comestible product based upon the weight, volume and other characteristics of that product.

The present invention defines a process for determining the volume of any comestible product without exposing the product to fluids, chemicals, or heat. The invention utilizes the simple relationship between pressure and volume of a gas (commonly known as Boyle's Law and expressed as $P_1*V_1=P_2*V_2$) to compute the volume of a solid object. This method is especially useful in whole poultry production where the carcass cavity is mostly hidden from visual and other scanning methods.

In another embodiment of the invention, a method for determining percentage bone content in a comestible product is provided by subjecting the comestible product to non-visible radiation. An amount of absorbed non-visible radiation by the comestible product is detected and an internal image of at least one bone structure of the comestible product based upon the detected absorbed radiation is constructed. The image is transmitted to a control module that calculates a percentage of bone material in the comestible product based upon the internal image of the at least one bone structure.

The products referred to in this invention can be comestible products such as whole carcasses or cuts from carcasses of beef, pork, sheep, chickens, turkeys or fish. The object to be measured is placed in an airtight chamber of known volume. The pressure in the chamber is recorded upon closure of the chamber. The volume of the chamber is modified (preferably decreased) by a known amount with a piston, bellows, or some other high-speed mechanical or electromechanical device, and the resultant chamber pressure is recorded. These values can be used to determine the precise volume of the object in the chamber.

The objects described herein are primarily cuts and carcasses of beef, pork, poultry and fish. However, the same techniques can be used in other industries including, but not limited to, fruits, vegetables, grains and other processed foods. In fact, any industry that depends on high-volume manufacturing or processing that wishes to determine the content value of a particular ingredient of an intermediate or finished product can utilize the methods and devices of the present invention.

In contrast to previous methods for determining the volume of a meat cut which measured the volume of the meat cut directly, the present invention is capable of precisely measuring the volume of a whole animal carcass. This is accomplished primarily by designing volumetric measurement chambers that are able to accommodate either a cut of meat or an entire carcass. Furthermore, the present invention is designed to measure the volume of an object by utilizing only a single measurement chamber, thus eliminating the need to have a second measurement chamber attached to the first chamber.

BRIEF DESCRIPTION OF THE DRAWINGS

FIG. 1 depicts a diagram of the volumetric determination system for the static case.

FIG. 2 depicts a diagram of the fat content determination assembly.

DETAILED DESCRIPTION OF THE PREFERRED EMBODIMENTS

The following discussion assumes familiarity of one skilled in the art. Assume, for example, the initial pressure in a chamber is $P_1$, which occurs when the object to be measured is enclosed within the chamber. $P_1$ is probably the same pressure as the air outside the chamber, but this is not a necessary assumption for this invention. The volume in the chamber, which is precisely known, is denoted as $V_C$ and can be expressed as the sum of the volume of the object and the volume of the gas in the chamber.

$$V_C=V_O+V_G \quad \text{(equation 1)}$$

Where:

$V_C$=volume of measurement chamber
$V_O$=volume of object to be measured
$V_G$=volume of gas in chamber This invention uses decreasing volume (which increases the pressure) to determine the volume of the gas in the chamber. The volume of the object, therefore, will be:

$$V_O=V_C-V_G \quad \text{(equation 2)}$$

As gas in a space is decreased in volume, for example, the pressure within the space increases. This relationship of volume to pressure for a gas is known as Boyle's Law and can be expressed as:

$$P_1*V_1=P_2*V_2 \quad \text{(equation 3)}$$

Where:

$P_1$=initial pressure of gas in chamber
$P_2$=pressure of gas in chamber after volume is decreased
$V_1$=original volume of gas in chamber
$V_2$=final volume of gas in chamber There are two key factors not accounted for in equation 3—temperature and absorption. As a volume of gas is compressed, its temperature will rise. In addition, the cut of meat being measured will absorb some of the compressed gas. For a given volumetric measurement operation, all cuts of meat will be roughly the same size and will occur within equivalent amounts of time. Thus, the temperature increase of the gas and the absorption of the gas by the cut of meat will be roughly equivalent for all objects being measured. As such, it is possible to empirically determine a constant $K_V$ that can be used to modify equation 3 as:

$$P_1*V_1=K_V*P_2*V_2 \quad \text{(equation 4)}$$

If a piston with a displacement of volume $V_P$ is utilized the final volume of the gas $V_2$ can be expressed as the initial volume $V_1$ less the piston displacement volume $V_P$.

$$V_2 = V_1 - V_P \qquad \text{(equation 5)}$$

Combining equations 4 and 5 and solving for $V_1$ yields:

$$K_V * P_2 * V_P V_1 = K_V * P_2 - P_1 \qquad \text{(equation 6)}$$

Equating $V_1$ from equation 6 to $V_G$ in equation 2 yields the equation for the volume of the object being measured:

$$K_V * P_2 * V_P V_O = V_C - K_V * P_2 - P_1 \qquad \text{(equation 7)}$$

Where $V_C$ is the volume of the chamber before the piston is engaged. One skilled in the art could modify equation 7 whereby the value of $V_C$ is the volume of the chamber after the piston is engaged.

Thus, to determine the volume of the object, the object is enclosed in an airtight chamber and the initial pressure $P_1$ is measured. A known modification in the volume of gas is introduced to the chamber, causing a change in gas pressure. The new pressure $P_2$ is measured. All values in equation 7 are known, so $V_O$ can be precisely computed.

This method works best when the volume of the object is a large percentage of the volume of the chamber. This ensures that small volume changes will cause relatively large changes in gas pressure.

The constant $K_V$ will depend on the type of gas used and its temperature. In practice this invention uses atmospheric air from within the processing facility in order to reduce the cost of operation for the system. Preferably, at least one environmental sensor is provided to measuring a quality of the atmospheric air selected, such as humidity, barometric pressure, or any combination and the output of the environmental sensor(s) is used to adjust the calculations and/or modify the process. Alternatively, the entire object measurement mechanism could be enclosed within a climate-controlled housing that maintained a constant temperature and utilized a known mixture of gas. These are precautions that should be considered if the volumes of the objects to be measured are expected to vary across a wide range instead of a more narrow range.

The volumetric measurement system is precise as long as pressure can be precisely determined and the volume of the piston displacement is exactly known. In practice, there will be some error in the pressure sensor(s) and some degree of error in the volume change caused by the piston displacement. To overcome these realistic limitations, multiple pistons (or other mechanical or electromechanical displacement mechanism) could be added to the chamber and associated pressure measurements can be made. One skilled in the art can expand the derivation of equation 7 to account for multiple piston movements and associated pressure measurements performed in either a sequential or additive scheme.

Fat Content Determination for Boneless Objects

Precise fat content can be determined for cuts or carcasses that contain fat and lean as well as those that contain fat, lean and bone. The upcoming discussion will cover the fat/lean case, with the bone case being left for later.

Assume we know the precise volume and mass of a cut of meat that contains lean and fat. The mass of the object can be expressed as:

$$M_O = D_F * V_F + D_L * V_L \qquad \text{(equation 8)}$$

Where:
DF=density of fat
$D_L$=density of lean
$V_F$=volume of fat
$V_L$=volume of lean The total volume of the meat can be expressed as the sum of the volume of the fat and the volume of the lean:

$$V_O = V_F + V_L \qquad \text{(equation 9)}$$

Combining equations 8 and 9 and solving for $V_F$ or $V_L$ yields:

$$V_F = \frac{M_O - D_L * V_O}{(D_F - D_L)} \qquad \text{(equation 10)}$$

$$V_L = \frac{M_O - D_F * V_O}{(D_L - D_F)} \qquad \text{(equation 11)}$$

$$\% \text{ fat by volume} = \frac{V_F}{V_O} \qquad \text{(equation 12)}$$

Since the density of fat and lean are well known within each particular industry for their products, knowing the precise mass and volume of a cut or carcass allows processors to accurately determine fat content for boneless products.

Fat Content Determination for Boned Objects

Products that contain bones are more difficult, but the problem of determining fat content can be reduced to the case of fat/lean presented earlier. For specific cuts of meat, assumptions can be made about the bone content. For example, a side of beef will contain a discrete number of bones whose mass and volume will correlate to the mass and volume of the side of beef. The volume of bone content can be expressed as:

$$V_B = K_B * V_O \qquad \text{(equation 13)}$$

Where:
$V_B$=volume of bone in an object
$V_O$=volume of object
$K_B$=constant representing the % of bone in the object $K_B$ will vary according to the type of animal and according to the cut of meat, poultry or fish. In practice, $K_B$ will not be a constant for different sizes of the same cut or carcass. Smaller animals will probably have $K_B$ values that are higher than large animals. For example, two different chickens may have identical volumes, but one chicken may have larger bones. In this case it would be desirable to adjust $K_B$ to account for the larger or smaller boned birds.

One technique is to measure the cross-section of a bone that gives insight into the "largeness" of the bones. If, for example, the diameter of the leg bone of a chicken is a key indicator of the percentage of the chicken volume that contains bone, the bone diameter in the production environment can be measured to determine the $K_B$ value, or the percent of bone. The volume of the boned object is expressed as:

$$V_O = V_F + V_L + V_B \qquad \text{(equation 14)}$$

Where:

$V_O$=volume of object being processed
$V_F$=volume of fat in an object
$V_L$=volume of lean in an object
$V_B$=volume of bone in an object The mass of the boned object can be expressed as:

$$M_O = D_F * V_F + D_L * V_L + D_B * V_B \quad \text{(equation 15)}$$

Where:
$M_O$=mass of object being processed
$D_F$=density of fat in an object
$D_L$=density of lean in an object
$D_B$=density of bone in an object Combining equations 13, 14 and 15 and solving for $V_F$ yields:

$$V_F = \frac{M_O - D_B * K_B * V_O + D_L * V_O * (K_B - 1)}{(D_F - D_L)} \quad \text{(equation 16)}$$

The indicator of $K_B$ for an animal type and cut type can be determined from an exposed section of bone or an encapsulated bone. For exposed bones, non-contact visual techniques can be used to make the precise measurement. For encapsulated bones, X-ray or some other non-visible spectrum radiation and sensor can be used to determine the bone size or thickness. For visible bones, image capture technology using ambient or artificial light can be utilized to produce an image for analysis of bone size. The $K_B$ value for an animal type, cut type and characteristic bone thickness can be determined by an algebraic formula, by values in a lookup table, or any other means of extracting empirical data.

The techniques presented herein allow for the implementation of precise volumetric determination in high-speed production facilities. Implementations of the preferred embodiments can be utilized with throughput as low as one piece per minute and can achieve speeds as high as several thousand pieces per minute.

Preferred Embodiment for Volume Determination—Static Case

FIG. 1 shows a chamber for the precise measurement of volume for a cut of meat. The object to be measured 10 is a whole chicken carcass, although the object could be any comestible food product that has been through the skinning or de-feathering and evisceration stages of a production facility. In one embodiment, the carcass 10, which is suspended from a shackle 40 attached to a conveyor system 30 is placed within an airtight chamber 20 of known volume. The chamber 20 is formed in two sections: the front portion 21, which provides most of the encapsulation of the volume, and the lid 22, which encloses the back of the chamber. Other items that form part of the airtight chamber 20 are the face of the piston 50 and the collar 41 of the shackle 40.

After closure of the airtight chamber 20, the pressure within the chamber is measured with a pressure sensor 70, the value of which is assigned to $P_1$ in equation 7. Next, the piston 50 is engaged via an actuator 60, thus causing the volume within the chamber to decrease. The pressure is measured again with the pressure sensor 70, the value of which is assigned to $P_2$ in equation 7. Using equation 7, a control system or computer processor can determine the precise volume for the object 10 within the chamber 20.

The volume of the chamber 20 in this embodiment will be the volumetric space within the enclosed sections 21, 22 when the piston 50 is in the non-actuated state. The chamber 20 volume will also need to be adjusted for the volume of the shackle 40. For best results the volume within the empty chamber should be determined empirically to account for any variances that occur in the manufacturing of the chamber sections 21, 22, the installation of the pressure sensor 70, and the actual position of the non-actuated piston 50. This empirically determined empty chamber volume is assigned to $V_C$ in equation 7.

A control system or module 90 in the form of a programmable logic controller (PLC), microcontroller, microprocessor, computer processor and associated software or hardware control logic and associated firmware performs the measurement of the chamber 20 pressures, calculates whole bird 10 volumes using equation 7, and equates the computed volume to the particular bird 10 number for downstream processing. The pressure within the chamber 20 is transmitted from the pressure sensor 70 to the control module 90 via an interface 75. This interface 75 can be an analog signal medium, a digital electrical medium, a standard electrical interface like Ethernet, Universal Serial Bus (USB), IEEE 1394, an optical transport medium, a wireless connection, or any other mechanism for transporting information between two points.

The control module 90 can also control the actuation of the two sections 21, 22 of the measurement chamber 20 and can control the actuation of the piston 50 via the actuator interface 65. For high-speed production, however, the actuation of the chamber sections 21, 22, the actuation of the piston 50, and the measurement of pressure with the sensor 70 will most likely utilize mechanical methods to decrease the processing burden on the control module 90.

Information regarding the bird 10 tracking number 42 is transmitted to the control module 90 via an interface 80. The information can be in the form of a barcode that is scanned, a numerical indicator on the conveyor line 30, a mechanical counter mechanism, a magnetic strip that is sensed, or a variety of other methods. The interface 80 between the provider of the bird 10 tracking number 42 and the control module 90 can be an analog signal medium, a digital electrical medium, a standard electrical interface like Ethernet, Universal Serial Bus (USB), IEEE 1394, an optical transport medium, a wireless connection, or any other mechanism for transporting information between two points.

Preferred Embodiment for Volume Determination—Dynamic Case

FIG. 2 shows one embodiment of a full production system for the rapid determination of fat content for whole carcasses. The objects shown in FIG. 2 are whole chickens 10 that have been through the de-feathering and evisceration processes. In this embodiment, the birds 10 are each attached to a high-speed, overhead conveyor 30 moving at a constant rate 130. Each bird 10 is connected to the conveyor 30 by a shackle 40. However, it is not essential to the practice of this invention to use an overhead conveyor. Any type of conveyor system including, but not limited to, conveyor belts, bins or buckets that can transport the comestible products through the production assembly could also be used. The only requirement is that the comestible product must at some point be contained within an airtight volumetric determination chamber.

In one embodiment, the birds 10 are first weighed as they pass the scale 100, although other embodiments are possible where the birds 10, or other comestible products, are weighed at a different point in the assembly. Weight information is transmitted to the control module 90 via the scale interface 105.

In one embodiment, after the bird 10 is weighed, an image is taken by an X-ray emitter and collector assembly 110.

Other embodiments of the invention could have the X-ray image taken at another point in the assembly or some other form of non-visible radiation emissions could be utilized. The image is transmitted to the control module 90 via the image interface 115. The X-ray image is used to measure an internal image within the bird 10, such as the cross-section of one or more encapsulated bones on the bird 10, in order to determine the percentage of the carcass 10 that is bone material. Other embodiments of the present invention may employ visible spectrum, infrared or multi-spectral imaging or other automated, semi-automated or manual process for determining bone length or thickness.

Weighed and imaged birds 10 are next processed by the volumetric determination station 120. This assembly consists of a plurality of receiving chambers 20 that individually encompass each of the moving birds 10 in an airtight compartment 20, measure the initial chamber pressure, decrease the volume by actuating a piston 50, and measuring the resultant pressure. There are five distinct steps executed by the volumetric assembly 120 in the determination of fat content. The stages are driven by mechanical actuators and cams contained within the rotational assembly 120 that rotates at a constant rate 125.

Step one 150 consists of the encapsulation of the bird 10 in an airtight compartment 20 formed by a case 21 and a lid 22, where the lid 22 is a cavity carved into the body of the assembly 120. As the bird 10 rotates past stage one 150, a mechanical cam pushes up the case 21, thereby creating an airtight space 20. Each chamber has a pressure sensor 70 rigidly mounted to the wall of the chamber with externally exposed contacts. In other embodiments of the invention, the sensor 70 can be attached to the lid 22 or the piston 50. The pressure sensor 70 can be comprised of one or more of any number of types of pressure sensors, such as absolute pressure sensors, gauge-type pressure sensors, differential pressure sensors or sealed pressure sensors utilizing such different pressure sensing technologies such as piston measurement, mechanical deflection, strain gauge, semiconductor piezoresistive, piezoelectric, microelectromechanical systems (MEMS), vibrating elements, ultrasonic, solid state or variable capacitance.

Step two 160 consists of the measurement of the initial pressure within the chamber 20. The chamber 20 moves past the pressure measurement assembly 140 and comes in contact with a receiver 145, which allows the chamber pressure data to be transmitted from the pressure measurement assembly 140 to the control module 90 via the pressure interface 141.

In one embodiment, step three 170 utilizes a moving piston 50 to decrease the volume and increase the pressure within the chamber 20. In other embodiments of the invention, the volume could be decreased by a bellow or some other high-speed mechanical or electromechanical device. A mechanical cam is used to actuate the piston 50, which will remain activated until the final pressure measurement is taken. Alternatively, the volume of the chamber 20 could be increased by a moving piston 50 or the like, with appropriate changes made in the calculation of the end result.

Step four 180 consists of the measurement of the final pressure within the chamber. The chamber 20 moves past the pressure measurement assembly 140 and comes in contact with a receiver 146, which allows the chamber pressure data to be transmitted from the pressure measurement assembly 140 to the control module 90 via the pressure interface 141.

Step five 190 is where the two actuation cams are released, thus allowing the piston 50 and the case 21 to return to their original positions.

Upon completion of the processing within the five stages of the rotational assembly 120, the control module 90 has all of the raw information needed to compute the fat content of the bird 10. This raw information consists of a weight, one or more images of internal bone structures, an initial pressure measurement, and a final pressure measurement. These pieces of raw information all need to be associated with the same bird 10.

Several methods exist for maintaining relational timing within a processing facility that gathers product information from different points in time and space. The system described herein works most effectively when the assembly line 30 rate 130 is somewhat constant. A near constant rate allows fewer and lower-cost sensors to be utilized in the synchronization of bird 10 tracking numbers 42 between the various data gathering stations 100, 110, 160, 180, 200. Assembly lines 30 with higher variability in their production rates 130 will require more sophisticated sensors to ensure that the control module 90 can associate the incoming data elements with the appropriate bird 10.

FIG. 2 shows an optional shackle counter 200 that can be used to track the passing of shackles 30. This mechanism utilizes one or more optical sensors to note the movement of shackles 30 past the sensor 200. Multiple sensors 200 may be needed so a non-moving assembly line 30 with a swinging shackle 40 in front of the sensor does not fool the control module 90 into thinking that the assembly line 30 is actually in motion. The sensors 200 can be photo cells, one or more CCD or CMOS cameras, mechanical switches or laser-based switches.

The spacing between shackles 30 is known and will remain a constant for all birds 10. With the known spacing between birds and the periodic shackle counter 200 information being transmitted over the shackle sensor interface 205, the control module can keep track of the assembly line 30 rate 130 at any point in time.

In practice, there will likely be differences in the volumes of the chambers 20 on the processing assembly 120. The volumes of all of the enclosed chambers 20 will need to be determined empirically. Once the volumes are known, it may become necessary to associate pressure measurements with chamber 20 numbers. This problem is easily solved by having an electrical, mechanical, or some other indicator at or near each pressure sensor 70 contact that indicates the chamber 20 number. The chamber 20 number allows the control module to take the actual chamber 20 volume into account when computing the fat content for the bird 10.

The scale 100 weighs the birds 10 as they pass, but equation 16 utilizes the mass of an object. The weight of an object will relate to its mass according to:

$$W_O = g * M_O \qquad \text{(equation 17)}$$

Where:

$W_O$=weight of an object $M_O$=mass of an object g=gravitational constant

The gravitational constant within the processing facility will be stored in the control module 90 so weight information from the scale 100 can be converted to the mass of the bird 10.

Once the fat content calculation is made for each bird 10, the information can be forwarded to a downstream process to make routing or processing decisions based on the bird's 10 fat content. The control module 90 preferably has a mechanism to communicate the bird 10 tracking number 42 and its associated fat content to this downstream process 210. Several methods exist for communicating this tracking information. One commonly used technique is to have periodic "reference shackles" that carry some characteristic marking 220. These reference shackles can be used to communicate with the downstream process by relating bird 10 tracking numbers 42 relative to a reference shackle 220.

The embodiments shown in FIGS. 1 and 2 utilize a piston 50 that is actuated to cause a volume decrease within the chamber 20. Several other methods can be utilized to decrease volume within the chamber 20 including, but not limited to, bellows, slides, and moving chamber walls. Additionally, the pressure may be changed within the chamber 20 by forcing a known volume of gas into the chamber 20. The volume of gas forced into the chamber 20 would be associated with $V_P$ in equation 16.

The embodiments shown in FIGS. 1 and 2 utilize increasing pressure to compute volume. The system can also utilize decreasing pressure to achieve similar results. Either by removing a known quantity of gas or by increasing the size of the chamber 20, the resulting pressure will be lower than the initial pressure, but the process will still produce accurate volumetric determination.

Determination of the Constant $K_B$

The constant for the percentage of bone in an object ($K_B$) will depend on the type of animal, the cut of meat, the relative size of the cut, and the size of the bones. Each assembly line will be implemented to process a particular cut of meat. The determination of $K_B$ for a cut of meat will begin with the detailed analysis of several representative "samples" for that particular cut. For example, an assembly line has been implemented to determine fat content for sides of beef. Several sides of beef are weighed and subjected to destructive testing to determine their percent of bone content. The statistical results will be used to arrive at values for $K_B$ that relate to the carcass weight.

Two sides of beef with similar weights may contain different bone content due to the "largeness" of the bones. During destructive testing, several bone parameters are measured to determine which bones provide the best indicators for bone content. Statistical analysis will determine the proper bone(s) to be utilized within the factory to indicate values for $K_B$.

In practice the $K_B$ values utilized in fat content determination will be retrieved from a multi-variable lookup table contained within the control module. The variables used for $K_B$ lookup can include, but are not limited to, weight of cut, volume of cut, size of one or more bone cross-sections, or the length of one or more bones.

In processing facilities such as those used in poultry production, it is common for whole birds to have missing parts. For example, a turkey with a missing wing will have a different $K_B$ value than a turkey with no missing parts. The system described herein can make determinations about the missing parts and adjust $K_B$ accordingly. The system will need to have empirical knowledge about the various missing parts and how their absence impacts $K_B$. The destructive testing described earlier should account for various missing parts and add the appropriate variables to the multi-variable lookup table for $K_B$.

In extreme circumstances a section of a measured object will be missing that does not correspond to a variable in the $K_B$ lookup table. For example, a chicken may be processed that contains only two legs and a portion of the torso. Since the percentage of the torso remaining does not provide a good indicator of the bone percentage for this partial bird, the system cannot accurately compute the percentage of bone content. In these circumstances the system must be capable of informing the downstream equipment that the fat content determination is not accurate and the partial bird must receive some special handling.

Several of the $K_B$ variables, like bone cross section, bone length and missing part determination require input from two-dimensional sensors. For characteristics that are visible at or above the surface of the cut of meat, visible spectrum digital cameras can be used for image acquisition. For characteristics that lie below the surface of the cut, techniques like X-ray, ultrasonic radiation, or some other form of surface penetrating radiation and detection will be required for image analysis. The determination of missing pieces on a cut and the measurement of bone length or thickness can be performed with imagery from different input sources.

Although it is not practical in high-speed production environments, bone size information, missing parts information or other information necessary to compute $K_B$ could be identified by humans inspecting the cuts of meat as they pass by an inspection station. In this embodiment, manually generated information would be entered into a computer terminal, for example, to associate the particular information to a cut number so the processing system could make the association of the manually supplied information with the proper cut of meat.

Determination of the Constant $K_V$

The constant $K_V$ is utilized to adjust for temperature changes and gas absorption not accounted for in equation 3. Since all cuts of meat will be roughly equivalent in size and will be at the same stage within the production facility, each cut of meat on the line will experience an equivalent temperature increase and gas absorption rate. As a result, the constant $K_V$ will truly be a constant value for a production line with a defined cut of meat.

Since cuts of meat come in different sizes and absorb gases differently, each assembly line that processes different animals or different cuts from an animal will have different $K_V$ values. In addition, the size and design of the chamber will impact the $K_V$ value for a given production line.

The value for $K_V$ will likely remain constant throughout a processing shift. Changes from day-to-day, however, can impact $K_V$. For example, humid air will compress differently than dry air. To account for this, it may be necessary to calibrate the $K_V$ value prior to starting a production run. This calibration process could involve placing objects of known volume on the shackles and running them through the volumetric measurement process. The value of $K_V$ could be adjusted so the measured pressure values produce the volumetric result that equals the know volume of the objects.

A more realistic approach for adjusting $K_V$ values for variables like humidity or ambient air temperature would be to provide sensor inputs to the control module that measure the variables that impact $K_V$. The control module could then determine the $K_V$ value by accessing a lookup table that contained pre-determined values for $K_V$ with respect to the known variables.

Other Applications

Although the preferred embodiment of the present invention has been described with respect to meat products, it will be recognized that content analysis of a variety of other kinds of comestible foodstuff products can also be evaluated and determined using the methods and apparatus of the present invention. For example, a watermelon buyer may wish to know the percentage of rind for a batch of watermelons. While it is possible for a buyer to destructively test a few of the melons to determine an estimate of rind content for a given batch of melons, the present invention allows all of the melons to be measured volumetrically and weighed so the precise rind content for each melon would be known. The melon buyer could use this information to determine the price to pay the grower and could assign grades to each melon in order to maximize the profit margin of the product sold to consumers.

As another example, assume that a bread manufacturer purchases wheat directly from growers, but utilizes only wheat hearts in the production of bread. The manufacturer could pay the grower based on the percentage of wheat hearts or the actual weight of wheat hearts contained within a shipment of wheat. In this example the bread manufacturer would use the known densities of wheat hearts and wheat chaff to determine heart content.

Yet another example would be to determine the volume of flavored chips in processed cookies. By measuring the weight and volume of finished cookies and knowing the densities of the cookie and chips, the percent of chips by volume or weight can be determined for the finished product. The cookie manufacturer could use this information to sort cookies into their percent chip categories or could be used as a quality control check for the mixing and baking process.

The above description has been of preferred embodiments of the present invention and one skilled in the art will realize that numerous modifications may be made without departing from the spirit and scope of the invention.

What is claimed:

1. A device for measuring a volume of a comestible product comprising:
   a plurality of single selectively sealable volumetric measurement chambers of known volume designed to enclose a comestible product, each measurement chamber designed to enclose one of a series of similar comestible products;
   means for detecting a change in pressure inside each volumetric measurement chamber;
   means for changing the volume of each volumetric measurement chamber, where the means for changing the volume is operably connected to that chamber; and
   control means operably connected to the plurality of single selectively sealable volumetric measurement chambers and the means for detecting the change in pressure inside each chamber for controlling operation of the device so as to determine a volume for each of the series of similar comestible product based upon the change in pressure.

2. An automated method for determining a volume of a comestible product comprising the steps of:
   enclosing a series of similar comestible products in a plurality of single volumetric measurement chambers;
   determining an initial pressure inside the volumetric measurement chamber;
   changing the volume of the volumetric measurement chamber by a known volume;
   determining a final pressure inside the volumetric measurement chamber after the volume has been changed; and
   determining a volume of the comestible product based upon the known changed volume of the chamber, the initial pressure of the chamber and the final pressure of the chamber,
   wherein the step of enclosing the comestible product is accomplished for one of the series of similar comestible products by enclosing that comestible product in an open one of the plurality of measurement chambers while the remaining steps are performed on at least another of the plurality of measurement chambers that has already been enclosed with another of the series of similar comestible products.

* * * * *